US008968778B2

(12) United States Patent
Peroutka et al.

(10) Patent No.: US 8,968,778 B2
(45) Date of Patent: *Mar. 3, 2015

(54) THREO-DOPS CONTROLLED RELEASE FORMULATION

(71) Applicant: Lundbeck NA Ltd., Wilmington, DE (US)

(72) Inventors: Stephen Peroutka, Princeton, NJ (US); James Swarbrick, Pinehurst, NC (US)

(73) Assignee: Lundbeck NA Ltd., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,776

(22) Filed: May 10, 2013

(65) Prior Publication Data

US 2013/0243875 A1 Sep. 19, 2013

Related U.S. Application Data

(63) Continuation of application No. 13/418,410, filed on Mar. 13, 2012, now Pat. No. 8,460,705, which is a continuation of application No. 11/698,974, filed on Jan. 29, 2007, now Pat. No. 8,158,149, which is a continuation of application No. 10/556,399, filed as application No. PCT/US2004/014770 on May 12, 2004, now abandoned.

(60) Provisional application No. 60/469,634, filed on May 12, 2003.

(51) Int. Cl.

| A61K 9/22 | (2006.01) |
| A61K 9/52 | (2006.01) |
| A61K 31/195 | (2006.01) |
| A61K 9/00 | (2006.01) |
| A61K 9/16 | (2006.01) |
| A61K 9/20 | (2006.01) |
| A61K 9/28 | (2006.01) |
| A61K 9/48 | (2006.01) |
| A61K 31/198 | (2006.01) |

(52) U.S. Cl.

CPC ............ *A61K 9/0002* (2013.01); *A61K 9/1611* (2013.01); *A61K 9/1623* (2013.01); *A61K 9/1635* (2013.01); *A61K 9/1652* (2013.01); *A61K 9/2054* (2013.01); *A61K 9/2077* (2013.01); *A61K 9/2866* (2013.01); *A61K 9/4866* (2013.01); *A61K 31/198* (2013.01)

USPC ........................... 424/468; 424/497; 514/567

(58) Field of Classification Search

CPC . A61K 9/1611; A61K 9/1623; A61K 9/1635; A61K 31/198; A61K 9/2077

USPC ................................... 424/497, 468; 514/567

See application file for complete search history.

(56) References Cited

U.S. PATENT DOCUMENTS

| 3,920,728 A | 11/1975 | Hegedüüs et al. |
| 4,246,428 A | 1/1981 | Ohashi et al. |
| 4,256,108 A | 3/1981 | Theeuwes |
| 4,265,874 A | 5/1981 | Bonsen et al. |
| 4,319,046 A | 3/1982 | Vacek |
| 4,330,558 A | 5/1982 | Suzuki et al. |
| 4,421,767 A | 12/1983 | Palfreyman et al. |
| 4,480,109 A | 10/1984 | Ohashi et al. |
| 4,497,826 A | 2/1985 | Narabayashi et al. |
| 4,529,603 A | 7/1985 | Mori et al. |
| 4,562,263 A | 12/1985 | Ohashi et al. |
| 4,571,333 A | 2/1986 | Hsiao et al. |
| 4,647,587 A | 3/1987 | Katsube et al. |
| 4,690,949 A | 9/1987 | Yoshida et al. |
| 4,699,879 A | 10/1987 | Umezawa et al. |
| 4,863,742 A | 9/1989 | Panoz et al. |
| 4,952,402 A | 8/1990 | Sparks et al. |
| 4,963,590 A | 10/1990 | Bäckström et al. |
| 5,164,193 A | 11/1992 | Okada et al. |
| 5,165,937 A | 11/1992 | Santus et al. |
| 5,240,930 A | 8/1993 | Al-Damluji |
| 5,266,596 A | 11/1993 | Yokokawa et al. |

(Continued)

FOREIGN PATENT DOCUMENTS

| EP | 0237 929 | 9/1987 |
| EP | 0506384 | 9/1992 |

(Continued)

OTHER PUBLICATIONS

Agmo et al., "A Rat Model of Distractibility: Effects of Drugs Modifying Dopaminergic, Noradrenergic and GABA Ergic Neurotransmission," *Journal of Neural Transmission*, 1997, pp. 11-29, Vo. 104, No. 1. http://www.springerlink.com/content/n66254211q511485/.

Bennett, et al., "A Peripheral Mononeuropathy in Rat That Produces Disorders of Pain Sensation Like Those Seen in Man," *Pain*, 1988, pp. 87-107, vol. 33, No. 1.

Bradley et al., "Orthostatic Hypotension," *American Family Physician*, 2003, pp. 2393-2398, vol. 68, No. 12.

Brzostowska et al., "Phenylcarbamates of (−)-Eseroline, (−)-N1-Noreseroline and (−)-Physovenol: Selective Inhibitors of Acetyl and, or Butyrylcholinesterase", *Medical Chemistry Research*, 1992, pp. 238-246, vol. 2, No. 4.

Calkins et al., "Relationship Between Chronic Fatigue Syndrome and Neurally Mediated Hypotension," *Cardiology in Review.* (1998), pp. 125-134, vol. 6, No. 3.

Cryan et al., "Norepinephrine-Deficient Mice Lack Responses to Antidepressant Drugs, Including Selective Serotonin Reuptake Inhibitors," *PNAS*, 2004, pp. 8186-8191, vol. 101, No. 21. www.pnas.org./cgi/doi/10.1073/pnas.0401080101.

Dableh et al., "Antidepressant-like Effects of Neurokinin Receptor Antagonists in the Forced Swim Test in the Rat," *European Journal of Pharmacology*, 2005, pp. 99-105, vol. 507.

(Continued)

Primary Examiner — Blessing M Fubara
(74) Attorney, Agent, or Firm — Womble Carlyle Sandridge & Rice, LLP

(57) ABSTRACT

The present invention relates to pharmaceutical formulations for the controlled delivery of threo-3-(3,4-dihydroxyphenyl) serine (threo-DOPS) and derivatives of it. Such formulations can contain an extended or slow release component that maintains therapeutic concentration of threo-DOPS in the blood plasma over a prolonged time period. They can be further combined with an immediate release formulation to produce a product that, when administered to a patient in need thereof, results in substantially steady levels of active drug, eliminating the sharp peaks and troughs in blood plasma drug levels experienced with the existing threo-DOPS formulations.

42 Claims, No Drawings

(56) References Cited

U.S. PATENT DOCUMENTS

| | | | |
|---|---|---|---|
| 5,288,898 | A | 2/1994 | Umezawa et al. |
| 5,364,620 | A | 11/1994 | Geoghegan et al. |
| 5,549,912 | A | 8/1996 | Oshlack et al. |
| 5,616,618 | A | 4/1997 | Takagi |
| 5,645,858 | A | 7/1997 | Kotwal et al. |
| 5,656,669 | A | 8/1997 | Nishino |
| 5,739,387 | A | 4/1998 | Oda et al. |
| 5,864,041 | A | 1/1999 | Oda et al. |
| 5,871,776 | A | 2/1999 | Mehta |
| 6,033,993 | A | 3/2000 | Love, Jr. et al. |
| 6,066,339 | A | 5/2000 | Stark et al. |
| 6,143,314 | A | 11/2000 | Chandrashekar et al. |
| 6,150,412 | A | 11/2000 | Pystynen et al. |
| 6,228,398 | B1 | 5/2001 | Devane et al. |
| 6,365,343 | B1 | 4/2002 | McNally |
| 6,387,936 | B1 | 5/2002 | Blanchard-Bregeon et al. |
| 6,512,136 | B1 | 1/2003 | Benes et al. |
| 6,610,324 | B2 | 8/2003 | Stoll |
| 6,610,690 | B2 | 8/2003 | Wong et al. |
| 6,653,325 | B2 | 11/2003 | Svensson |
| 6,667,060 | B1 | 12/2003 | Vandecruys et al. |
| 6,703,424 | B2 | 3/2004 | Levin et al. |
| 6,746,688 | B1 | 6/2004 | Kushnir et al. |
| 6,929,801 | B2 | 8/2005 | Klose et al. |
| 6,992,110 | B2 | 1/2006 | Kranzler et al. |
| 7,465,462 | B1 | 12/2008 | Jeary et al. |
| 8,158,149 | B2 * | 4/2012 | Peroutka et al. ............... 424/468 |
| 8,460,705 | B2 * | 6/2013 | Peroutka et al. ............... 424/468 |
| 2001/0003588 | A1 | 6/2001 | Sauer et al. |
| 2001/0007856 | A1 | 7/2001 | Nishino |
| 2001/0033866 | A1 | 10/2001 | Ogorka et al. |
| 2001/0047032 | A1 | 11/2001 | Castillo et al. |
| 2002/0177593 | A1 | 11/2002 | Ishihara et al. |
| 2003/0181509 | A1 | 9/2003 | Hinz |
| 2004/0013620 | A1 | 1/2004 | Klose et al. |
| 2004/0152760 | A1 | 8/2004 | Castillo et al. |
| 2005/0043408 | A1 | 2/2005 | Yeboah et al. |
| 2005/0096387 | A1 | 5/2005 | Verheijen et al. |
| 2005/0233010 | A1 | 10/2005 | Satow |
| 2006/0035976 | A1 | 2/2006 | Peroutka |
| 2007/0004639 | A1 | 1/2007 | Kane et al. |
| 2007/0122479 | A1 | 5/2007 | Peroutka et al. |

FOREIGN PATENT DOCUMENTS

| | | |
|---|---|---|
| GB | 2 200 109 A | 7/1988 |
| WO | WO 2004/032844 A2 | 4/2004 |
| WO | WO 2005/085178 A | 9/2005 |
| WO | WO 2007/112014 A2 | 10/2007 |
| WO | WO 2008/003028 A2 | 1/2008 |

OTHER PUBLICATIONS

Dhir et al., "Effect of Addition of Yohimbine (Alpha-2-Receptor Antagonist) to the Antidepressant Activity of Fluoxetine or Venlafaxine in the Mouse Forced Swim Test," *Pharmacology,* 2007, 239-243, vol. 80.

Edvinsson et al., "Effect of Exogenous Noradrenaline on Local Cerebral Blood Flow After Osmotic Opening of the Blood-Brain Barrier in the Rat," *J. Physiol.,* 1978, pp. 149-156, vol. 274.

Flippen-Anderson et al., Thiaphysovenol Phenylcarbamates: X-ray Structures of Biologically Active and Inactive Anti cholinesterase Agents, *Heterocycles,* 1993, pp. 79-86, vol. 36, No. 1.

Freeman et al., "The Treatment of Orthostatic Hypotension with Dihydroxyphenylserine", *Clinical Neuropharmacology,* 1991, pp. 296-304, vol. 14, No. 4.

Goldstein, "L-Dihydroxyphenylserine (L-DOPS): A Norepinephrine Prodrug," *Cardiovascular Drug Reviews,* 2006, pp. 189-203, vol. 24, No. 3-4.

Goto et al., "Depression in Multiple System Atrophy: A case Report,"*Psychiany and Clinical Neurosciences,* 2000, pp. 507-511, vol. 54.

Greig et al. "Phenserine and Ring C Hetero-Analogues: Drug Candidates for the Treatment of Alzheimer's Disease." *Medicinal Research Reviews.* (1995) vol. 15, No. 1, 3-31.

Hardebo et al., "A Comparative Study on the Uptake and Subsequent Decarboxylation of Monoamine Precursors in Cerebral Microvessels", *Acta Physiol Scand,* 1979, pp. 161-167, vol. 107.

He et al. "Thiaphysovenine and Carbamate Analogues:A New Class of Potent Inhibitors of Cholinesterases." *Medical Chemistry Research.* (1992) vol. 2, 229-237.

Henchcliffe et al. "Entacapone in the management of Parkinson's disease." The Neurological Institute, Colombia Presbyterian Medical Center. Expert Opin. Pharmacother: (2002) 3(7):957-963.

Ida et al., "Effects of L-Threo-3,4-Dihydroxyphenylserine on Orthostatic Hypotension in Hemodialysis Patients," *American Journal of Nephrology,* 2002, pp. 338-346, vol. 22, No. 4, Basel.

Joo, et al., "Cerebral Perfusion Abnormality in Narcolepsy with Cateaplexy," *Neurolmage,* 2005, pp. 410-416, vol. 28, No. 2.

Kato et al., "Reversal of the Reserpine-Induced Ptosis by L-Threo-3,4-Dihydroxy-Phenylserine (L-Threo-DOPS), A (−)-Norepinephrine Precursor, and Its Potentiation by Imipramine or Nialamide," *Naunyn-Schmiedeberg's Archies of Pharmacology,* 1986, pp. 243-246, vol. 332, No. 3, Berlin.

Kato et al., "Studies on the Activity of L-Threo-3,4-Dihydroxyphenylserine (L-DOPS) As a Catecholamine Precursor in the Brain, Comparison With Taat of L-DOPA," *Biochemical Pharmacology,* 1987, pp. 3051-3057, vol. 36, No. 18, Great Britain.

Kawabata et al., "The Noradrenaline Precursor L-Threo-3,4-Dihydroxyphenylserine Exhibits Antinociceptive Activity Via Central Alpha-Adrenoceptors in the Mouse," *Br J. Pharmacol.* 1994, pp. 503-508, vol. 111, No. 2, Japan.

Kaufman et al., Norepinephrine Precursor Therapy in Neurogenic Orthostatic Hypotension., Circulation 2003;108;724-728; originally published online Jul. 28, 2003; DOI:10.1161/01.CIR.0000083721. 49847.D7.

Kim et al., "Methylphenidate Increased Regional Cerebral Blood Flow in Subjects with Attention Deficit/Hyperactivity Disorder," *Yonsei Medical Journal,* 2001, pp. 19-29, vol. 42, No. 1.

Lahiri et al. "Cholinesterase Inhibitors, β-Amyloid Precursor Protein and Amyloid & Peptides in Alzheimer's Disease." *Acta Neurologica Scandinavia.* (Dec. 2000) vol. 102 (s176), 60-67.

Lamberti et al., "Antidepressant-like Effects of Endogenous Histamine and of Two Histamine $H_1$ Receptor Agonists in the Mouse Forced Swim Test,"*British Journal of Pharmacology,* 1998, pp. 1331-1336, vol. 123.

Lee et al., "Regional Cerebral Blood Flow in Children With Attention Deficit Hyperactivity Disorder: Comparison Before and After Methylphenidate Treatment," *Human Brain Mapping,* 2005, pp. 157-164, vol. 24, No. 3.

Lou et al., "Focal Cerebral Hypoperfusion in Children With Dysphasia and/or Attention Deficit Disorder," *Archives of Neurology,* 1984, pp. 825-829, vol. 41, No. 8.

Lyytinen et al., The Effect of Catechol-O-methyltransferase Inhibition with Entacapone on Cardiovascular Autonomic Responses in L-Dopa-treated Patients with Parkinson's Disease. Clinical Neuropharmacology, vol. 24, No. 1, pp. 50-57, 2001.

Martignoni et al., Cardiovascular dysautonomia as the cause of falls in Parkinson's disease, 2006, Parkinsonism and Related Disorders, vol. 12, pp. 195-204.

Mathias et al., "L-Threo-dihydroxyphenylserine(L-threo-DOPS; droxidopa) in the management of Neurogenic Orthostatic Hypotension: A Multi-National, Multi-Center, Dose-Ranging Study in Multiple System Atrophy and Pure Autonomic Failure,"*Clinical Autonomic Research: Official Journal of the Clinical Autonomic Research Society,* 2001.

www.merck.com, "Orthostatic Hypotension and Syncope," *The Merck Manual of Diagnosis and Therapy,* 1996, Sec. 16, Chapter 200.

Moldes et al. "The Actions of Dihydroxyphenylalanine and Dihydroxyphenylserine on the Sleep-Wakefulness Cycle of the Rat After Peripheral Decarboxylase Inhibition," *Br J Pharmacol,* 1975, pp. 101-106, vol. 54, No. 1.

Mori et al., "Effects of L-Erythro-3, 4-Dihydroxyphenylserine on Sleep-Wakefulness Patterns and Concentrations of Brain Catecholamines and Serotonin in Rats," *Jpn J Psychiany Neurol,* 1987, pp. 301-10, vol. 41, No. 2.

(56) References Cited

OTHER PUBLICATIONS

Movement Disorder Society, Movement Disorders "Drugs to Treat Autonomic Dysfunction in Parkinson's Disease." Movement Disorder Society vol. 17, Supp. 4, 2002, p. S103-S111.

Noto et al., "Effects of L-Threo- and Erythro-3,4-Dihydroxyphenylserine on Learning Performance and Concentrations of Brain Noradrenaline and Its Metabolites in Rats," *Pharmacol Biochem Behav.*, 1992, pp. 215-221, Vo. 43, No. 1.

Pei et al. "Total Synthesis of Racemic and Optically Active Compounds Related to Physostigimine and RingC Heteroanalogues from 3[-2'-(Dimethylamino0ethyl]-2,3-dihydro-5-methoxy-1, 3-dimentyl-1H-indol-2-ol." *Helvetica Chimica ACTA.* (1994) vol. 77.

Porsolt et al., "Behavioural Despair in Mice: A primary Screening Test for antidepressants," *Arch. Int. Pharmacodyn,* 1977, pp. 327-336, vol. 229.

Rowe et al., "Is Neurally Mediated Hypotension an Unrecognised Cause of Chronic Fatigue?"*The Lancet,* 1995, pp. 623-624, vol. 345.

Russell, "Advances in Fibromyalgia: Possible Role for Central Neurochemicals,"*Am J Med Sci.,* 1998, pp. 377-384, vol. 315, No. 6.

www.jnnp.bmjjournals.com, Schondorf, "Acetylcholinesterase Inhibition in the Treatment of Hypotension," *Journal of Neurology Neurosurgery and Pshychiatry,* 2003, pp. 1187, vol. 74, No. 9.

Singer et al, "Pyridostigmine Treatment Trial in Neurogenic Orthostatic Hypotension",2006, *Archives of Neurology.* vol. 63, No. 4, pp. 513-518. www.archneur.ama-assn.org.

Takagi et al., "Analgesic Effect of L-Threo-3,4-Dihydroxyphenylserine (L-DOPS) in Patients With Chronic Pain," *Eur Neuropsychopharmacol.,* 1996, pp. 43-47, vol. 6, No. 1, Japan.

Tanaka et al., "The Effects of the Noradrenaline Precursor, L-Threo-3,4-Dihydroxy-Phenylserine, in Children With Orthostatic Intolerance," *Clinical Autonomic Research,* 1996, pp. 189-193, vol. 6.

Toda et al., "Parkinson Disease Patient with Fibromyalgia: A Case Report" *Parkinsonism and Related Disorders,* 2007, pp. 312-312, vol. 13.

Tulen et al., "Sleeping With and Without Norepinephrine: Effects of Metoclopramide and D,L-Threo-3,4-Dihydroxyphenylserine on Sleep in Dopamine Beta-Hydroxylase Deficiency," *Sleep,* 1991, pp. 32-38, vol. 14, No. 1. The Netherlands.

Verhagen-Kamerbeek, et al. "Attenuation of Haloperidol-Induced Catalepsy by Noradrenaline and L-Threo-DOPS," *Journal of Neural Transmission. Parkinson's Disease and Dementia Section,* 1993, pp. 17-26, vol. 6. No. 1, Austria.

Yamamoto et al., "Pyridostigmine in Autonomic Failure: Can We Treat Postural Hypotension and Bladder Dysfunction With One Drug?" *Clinical Autonomic Research,* 2006, pp. 296-298, vol. 16, No. 4.

Yoshida et al., "Inhibitory Effects of L-Threo-DOPS on Electroshock Seizure in Mice," *Brain and Nerve,* 1989, pp. 567-573, vol. 41, No. 6, Japan.

Yu et al. "Novel Phenserine-Based-Selective Inhibitors of Butyrylcholinesterasefor Alzheimer's Disease." Reprinted with permission from*J. Med. Chem.*, May 20, 1999, 42, 1855-1861.

Yu et al. "Total Syntheses and Anticholinesterase Activities of (3aS)-N (8)-Norphysostigmine, (3aS)-N (8)-Norphenserine, Their Antipodal Isomers, andOther N (8)-Substituted Analogues." *J. Med. Chem.* (1997) vol. 40, 2895-2901.

Zern et al., "Effect of Increased Pancreatic Islet Norepinephrine, Dopamine and Serotonin Concentration on Insulin Secretion in the Golden Hamster," *Diabetologia,* 1980, pp. 341-346, vol. 18, No. 4, Berlin.

\* cited by examiner

THREO-DOPS CONTROLLED RELEASE FORMULATION

CROSS-REFERENCE TO RELATED APPLICATIONS

The present application is a continuation of U.S. patent application Ser. No. 13/418,410, filed Mar. 13, 2012, which is a continuation of U.S. patent application Ser. No. 11/698,974, filed Jan. 29, 2007, now U.S. Pat. No. 8,158,149, issued Apr. 17, 2012, which is a continuation of U.S. patent application Ser. No. 10/556,399, filed Nov. 10, 2005, which claims priority to International Patent Application No. PCT/US2004/014770, filed May 12, 2004, and U.S. Provisional Patent Application No. 60/469,634, filed May 12, 2003, the disclosures of which are incorporated herein by reference in their entireties.

DESCRIPTION OF THE INVENTION

The present invention relates to pharmaceutical formulations for the controlled delivery of threo-3-(3,4-dihydroxyphenyl)serine (threo-DOPS), and derivatives thereof. Threo-DOPE exists as the optically active L- and D-forms and the racemic DL form. The L-threo-DOPS is preferred for the purposes of this invention. Such formulations can contain an extended or slow release component that maintains therapeutic concentration of threo-DOPE in the blood plasma over a prolonged time period. They can be further combined with an immediate release formulation to produce a product that, when administered to a patient in need thereof, results in a rapid attainment of a therapeutic effect, followed by substantially steady levels of active drug, eliminating the sharp peaks and troughs in blood plasma drug levels experienced with the existing threo-DOPS formulations. These formulation are especially useful in the treatment of conditions associated with norepinephrine (NE) dysfunction, and which benefit from the controlled release of threo-3-(3,4-dihydroxyphenyl) serine compounds, such as the pain associated with migraines, and disorders associated with sympathetic nervous system dysfunction such as orthostatic hypotension, orthostatic intolerance, etc.

A pharmaceutical formulation of the present invention includes a controlled release pharmaceutical formulation, comprising: an effective amount of threo-3-(3,4-dihydroxyphenyl)serine, a derivative thereof, or a pharmaceutically-acceptable salt thereof, in an extended release form. A controlled release formulation can be effective for any desired period of time, e.g., oral dosage units can be produced that are effective for once-daily, twice a day (about every 12 hours), or three times (about every 8 hours) a day administration.

The phrase "controlled release" indicates that the release of the active ingredient is regulated or modulated to achieve a desired rate of delivery into the systemic circulation. A controlled release formulation can be pulsed, delayed, extended, slow, steady, immediate, rapid, fast, etc. It can comprise one or more release formulations, e.g. extended—and immediate-release components. For example, to prevent pain, such as the pain associated with migraine headaches, an oral controlled release formulation can comprise a plurality of components positioned in any suitable arrangement, e.g., comprising a "free" drug in a rapidly soluble polymer film on the outside of the dosage unit to achieve an immediate therapeutic effect, and an extended release delivery system in the core of the unit to produce steady state concentrations of drug to prevent recurrence of the pain. A formulation can be a composition of matter, a device, a patch, multi-layered or multi-configured products, etc.

The terms "extended release", "immediate release", etc., have their conventional meanings. An extended release composition is one in which the active ingredient is not released immediately in its active form, but is slowly and controllably discharged from the dosage unit. The kinetics of the extended release are influenced by the choice of the delivery system, amount of the active ingredient, dissolution rate of the drug, compartment in which release occurs (e.g., with oral delivery systems, this is the gastrointestinal tract), absorption of drug from the site of release into the systemic circulation, drug distribution from the systemic circulation, etc. An immediate release formulation can be used to deliver the equivalent of a "bolus" to the body, releasing the active form of the drug directly into the targeted physiological compartment (e.g. the GI tract) to achieve rapid systemic availability.

Any suitable extended release delivery system can be used in accordance with the present invention to achieve the slow release of threo-DOPS. Several are discussed below, but any effective system can be used without limitation.

1. Dissolution controlled release. Drug particles or granules that have a reasonable aqueous solubility, such as threo-DOPS, can be coated with, or embedded in, a slowly soluble material. The coated particles or granules can subsequently be compressed into tablets or filled into hard gelatin capsules. Drug can also be applied to the surface of non-pareil seeds, which can then be coated and formulated into either tablets or capsules.

Coating materials include, but are not limited to, shellacs, beeswax, glyceryl monostearate, glyceryl palmostearate, stearyl alcohol, ethylcellulose, cellulose acetate phthalate, acrylic resins, methacrylate hydrogels, methylmethacrylate, polymethacrylate, polylactic acid, polyvinyl chloride, polyvinyl chloride, polymethacrylate, hydroxypropylmethylcellulose, polyethylene glycols, carboxymethylcellulose, sodium carboxymethylcellulose, etc.

2. Diffusion controlled release. Two main types of diffusion controlled systems are typically used: reservoir devices and matrix devices. In a reservoir device, a water-insoluble polymeric material surrounds a drug-containing core, which can be a tablet, or particles or granules that are subsequently formulated into a tablet or a capsule. Materials used as coatings in reservoir devices include hydroxypropylcellulose/polyvinyl acetate combinations, polyethylene glycol/ethylcellulose combinations, ethylcellulose, and poly (hydroxymethacrylate).

With matrix devices, the drug is dispersed in an insoluble matrix consisting of such materials as hydrated methylcellulose, carnauba wax and stearyl alcohol combinations, carbopol, glyceryl tristearate, methyl acrylate/methyl methacrylate combinations, and polyvinyl chloride and polyethylene, alone and in combination.

3. Diffusion and dissolution controlled release. In this delivery system, the drug core is encased by a partially-soluble membrane. Dissolution of the soluble portion of the membrane facilitates diffusion of drug through the resultant pores of the polymer coat. An example of this type of coating system is ethylcellulose/methylcellulose combinations.

4. Ion-exchange resins. This approach is based on the presence of ions in the gastrointestinal tract which will exchange with the drug ions present in the resin. The drug-charged resin is prepared by mixing the resin with a solution of the drug, followed by washing and then drying to form particles or beads. These are then filled into gelatin capsules or suspended in an appropriate vehicle; prior to this step, they may be film-coated using one or more of the agents listed in sections 1 and 2 above. In one such system, drug-containing resin particles are coated with polyethylene 4000 and then with ethylcellulose.

5. pH-independent release. The addition of buffers to the drug delivery system can be utilized in such a concentration so as to cause the drug to be released at a rate that is independent on the pH in the gastrointestinal tract.

6. Osmotically controlled release. In this type of delivery system, a core containing the drug and an appropriate amount of an osmotically active salt is surrounded by a semipermeable membrane that is both rigid and non-swelling. The membrane is permeable to gastrointestinal fluid but impermeable to the drug in solution. Following administration, gastrointestinal fluids diffuse across the semipermeable membrane, thereby dissolving the drug and osmotically active salt to set up an osmotic pressure within the delivery system. Drug solution is then pushed through a laser-drilled orifice in to the gastrointestinal tract at a constant (zero order) rate until all of the osmotically active salt is depleted.

7. Altered density formulations. This approach relies on the formation of a low density, buoyant, drug-containing tablet matrix. As a result, the delivery system tends to remain floating on top of the stomach contents, dispensing drug in a uniform manner.

In an immediate release component, the release kinetics are largely dependent on the solubility of threo-DOPS. The active drug can be mixed with any conventional soluble excipient (such as lactose), or formulated with a soluble polymer that readily and directly dissolves in the targeted compartment (e.g., GI tract). The threo-DOPS can also be modified to improve its solubility, e.g., by physical (micronized to reduce particle size) treatment, the use of permeation enhancers, or chemical treatment.

Threo-3-(3,4-dihydroxyphenyl)serine (also known as threo-DOPS or droxidopa) is a synthetic amino acid precursor of NE (Freeman R., *Clin. Neuropharm.*, 14, 296-304, 1991). It has four stereoisomers, L-threo-DOPS, D-threo-DOPS, L-erythro-DOPS, and D-erythro-DOPS. Of the four, L-threo-DOPS is preferred, but a racemate can also be used. L-threo-DOPS is directly converted to NE via the actions of dopa decarboxylase (DDC) (also known as L-aromatic amino acid decarboxylase or AAAD). Peak plasma levels of L-threo-DOPS occur 3 hour after oral ingestion whereas peak NE levels occur 5 hours after ingestion. Increased plasma levels of both molecules remain at least 12 hours after oral administration of L-threo-DOPS(S Suzuki T, Higa S, Sakoda S, Ueji M, Hayashi A, Takaba Y, Nakajima A.; Eur J Clin Phainiacol 1982; 23(5):463-8). Specific uptake of threo-DOPS has also been demonstrated in microvessel preparations (Hardebo J E, Falck B, Owman C. Acta Physiol Scand 1979 October; 107(2):161-7).

Any effective amount of threo-3-(3,4-dihydroxyphenyl) serine can used, e.g., from about 10 mg to about 1000 mg per day, about 50 mg to about 700 mg per day, about 100 to about 500 mg per day, about 100 to about 300 mg per day, etc. An effective amount is a quantity of threo-DOPS that is useful for achieving the desired therapeutic effect, e.g., preventing pain, maintaining blood pressure, preventing the reoccurrence of a norepinephrine dysfunctional disorder. Effective amounts can be determined routinely, and may vary depending upon the age, health, gender, and weight of a patient, as well as the severity, frequency, and duration of the pain. The choice of the delivery system will also guide the selection of the amounts used. Amounts can be administered in multiple doses over the course of the day, e.g., in order to achieve a prophylactic effect, or a single dose in a hybrid extended/immediate release form.

Any suitable dosing interval can be used in accordance with the present invention. Extended delivery systems can be utilized to achieve a dosing interval, when orally administered, of once every 24 hours, once every 12 hours, etc. The dosage form/delivery system can be a tablet or a capsule suited for extended release, but a sustained release liquid or suspension can also be used. A controlled release pharmaceutical formulation can be produced which maintains the release of, and or peak blood plasma levels of, threo-3-(3,4-dihydroxyphenyl)serine, derivative thereof, or salt thereof, over a period of at least 8, 12, 16, 18, 20, 24 hours, etc. With this type of formulation, the threo-DOPS can be continuously released in such a way that it is available and effective for maintaining the nerve terminal pools of norepinephrine.

A dissolution controlled release delivery system can be utilized in accordance with the present invention to provide a controlled release pharmaceutical composition. This delivery system can typically contain one or more of the following constituents: 1) active drug; 2) slowly soluble coating/matrix material (see above, for examples); 3) granulating agent; 4) lubricant (e.g., magnesium stearate); 5) channeling agent (e.g., silicon dioxide); 6) surfactant (e.g., sodium lauryl sulfate, sodium taurocholate or a polysorbate); and 7) filler (e.g., lactose).

An extended release matrix can comprise any amount of matrix material that is necessary to delay the release of threo-DOPS into the systemic circulation, e.g., amounts can be as low as 5-100% of active drug, but can also be 2-, 3-, 5-, 10-fold more than active drug, depending upon the matrix material and the desired delivery kinetics. The active ingredient can be embedded in a matrix that retards dissolution, or the active ingredient can be coated with a material that has an effect on dissolution, or a combination of both.

As mentioned earlier, an immediate release component can be associated with the extended release component to form a multi-layered or combination system having properties of both. This type of controlled release system can provide an immediate bolus to facilitate the filling of the depleted nerve terminals with norepinephrine, and then a slow release component to maintain threo-DOPS in the circulating blood at levels effective to conserve nerve terminal norepinephrine pools and/or to prevent sympathetic nervous system dysfunction.

A controlled release formulation of threo-DOPS can comprise a quantity of an immediate release preparation of threo-DOPS (or derivatives thereof, or pharmaceutically active salts thereof) combined with a quantity of an extended (slow or delayed) release threo-DOPS (or derivatives thereof, or pharmaceutically active salts thereof). The immediate release component can obtain a maximal release of threo-DOPS within approximately 1-3 hours after administration, and then fall toward baseline levels. The extended release component can show a maximal release of threo-DOPS between approximately 6-24 hours after administration. The extended release component can contain multiple and different extended release formulations to broaden the time over which the threo-DOPS is available in active form in the blood stream, e.g., having extended components that have maximal release at 6 hours, 12 hours; and 18 hours, respectively. This can be accomplished by creating multi-layered or multi-component dosage units, where each layer or component displays different dissolution kinetics, or by mixing different immediate and extended release components in a single capsule or tablet.

Extended delivery systems can also be utilized that release active drug at roughly the same rate (e.g., zero-order kinetics) for the predetermined delivery period (6, 12, 18, 24 hours, etc.), e.g., using an osmotic delivery system. Effective amounts incorporated into each of the components can be determined routinely. For example, based on the total weight of threo-DOPS (active drug) in the dosage unit, from about 15-55% can be in the immediate release form and from about 45-85% can be in the extended and slow release form, e.g., about 35% in immediate form and 65% in extended release form Threo-3-(3,4-dihydroxyphenyl)serine can be prepared according to any suitable method. These processes include those described in, e.g., U.S. Pat. Nos. 4,480,109, 4,562,263 and 5,864,041. It can be used as a racemic or optically active isomer, e.g., L-threo-DOPS.

Pharmaceutically-acceptable salts of threo-3-(3,4-dihydroxyphenyl)serine can also be used, including addition salts, e.g., inorganic acids, such as hydrochloric acid, hydrobromic acid, and sulfuric acid, and organic acids, such as fumaric acid, citric acid, tartaric acid, and succinic acid.

Any pharmacologically active derivative of threo-3-(3,4-dihydroxyphenyl)serine can be used. These include, e.g., N-methyl-3-(3,4-dihydroxyphenyl)serine alkyl esters, such as N-methyl-D,L-threo-3-(3,4-dihydroxyphenyl)serine and N-methyl-L-threo-3-(3,4 dihydroxyphenyl)serine, lower alkyl esters, methyl esters, ethyl esters, n-propyl esters, isopropyl esters, etc., as described in U.S. Pat. No. 5,288,898.

In addition to the substances already mentioned, active agents can be further combined with any other suitable additive or pharmaceutically acceptable carrier. Such additives include any of the substances already mentioned, as well as any of those used conventionally, such as those described in *Remington: The Science and Practice of Pharmacy* (Gennaro and Gennaro, eds, $20^{th}$ edition, Lippincott Williams & Wilkins, 2000); *Theory and Practice of Industrial Pharmacy* (Lachman et al., eds., $3^{rd}$ edition, Lippincott Williams & Wilkins, 1986); *Encyclopedia of Pharmaceutical Technology* (Swarbrick and Boylan, eds., $2^{nd}$ edition, Marcel Dekker, 2002).

These are generally referred to herein as "pharmaceutically acceptable carriers" to indicate they are combined with the active drug and can be administered safely to a subject for therapeutic or prophylactic purposes. These include, but are not limited to, antioxidants, preservatives, dyes, tablet-coating compositions, plasticizers, inert carriers, excipients, polymers, coating materials, osmotic barriers, devices and agents which slow or retard solubility, etc.

The active agent of this invention can be in any suitable form, without limitation. Forms suitable for oral use, include, but are not limited to, tablets troches, lozenges, aqueous or oily suspensions, dispersible powders or granules, emulsions, hard or soft capsules, solutions, syrups and elixirs. Compositions intended for oral use may be prepared according to any method known to the art for the manufacture of pharmaceutical compositions.

The present invention relates to methods of treating a disease in a subject in need thereof, comprising: administering a controlled release pharmaceutical formulation, comprising an effective amount of threo-3-(3,4-dihydroxyphenyl)serine, a derivative thereof, or a pharmaceutically-acceptable salt thereof, in an extended release form. The term "treating" is used conventionally, e.g., the management or care of a subject for the purpose of combating, alleviating, reducing, relieving, improving, etc., a disorder or disease. Diseases that can be treated in accordance with the present invention include, but are not limited to, with sympathetic nervous system dysfunction, Asthma, Hypersensitivity cough, Allergic Rhinitis/nasal congestion, Anorexia Nervosa, Congestive Heart Failure, Chronic Fatigue Syndrome, Depression, Erectile dysfunction, Essential Tremor, Irritable Bowel Syndrome, Migraine, Obesity, Orthostatic Hypotension, Orthostatic Intolerance, Pain, Premenstrual Syndrome/Premenstrual Dysphoric Disorder, Reynaud's phenomenon, Reflex Sympathetic Dystrophy, Overactive/neurogenic bladder, etc.

The examples below illustrate tablet and capsule extended release formulations comprising threo-DOPS. Tablets can be made conventionally, e.g., as described in Tablet Manufacture, *Encyclopedia of Pharmaceutical Technology*, Marcel Dekker, Inc., 2002, Pages 2713-2732. Various diluents, granulating fluids, glidants, etc, are described therein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire disclosure of all patents and publications cited herein are hereby incorporated by reference in their entirety.

EXAMPLES

1. An extended release hydrophilic matrix formulation prepared by wet granulation using a high shear mixer and compressed into tablets containing:

| | |
|---|---|
| L-threo-DOPS | 100 to 800 mg |
| Hydroxypropylmethylcellulose (HPMC) | 5 to 45% |
| Lactose | 5 to 20% |
| Magnesium stearate | 0 to 1.5% |
| Silicon dioxide | 0 to 0.5% |
| Granulation fluid | q.s. |

The drug, polymer, and filler are dry blended in a high shear mixer for 5 minutes, at which time sufficient granulation fluid is added to produce a wet granulation that is subsequently dried, screened, blended with lubricant, and compressed to form tablets.

2. An extended release hydrophilic matrix formulation prepared by wet granulation using a high shear mixer and compressed into tablets, onto which is applied additional L-threo-DOPS dispersed in an immediate release polymeric film coat containing:

| | |
|---|---|
| L-threo-DOPS | 25 to 300 mg |
| Ethylcellulose | 0 to 5.0% |
| Hydroxypropylmethylcellulose | 0 to 3.0% |
| Triethyl citrate | 0 to 2.0% |
| Aqueous ethanol | q.s. |

The drug, polymer, and filler are dry blended in a high shear mixer for 5 minutes, at which time sufficient granulation fluid is added to produce a wet granulation that is subsequently dried, screened, blended with lubricant, and compressed to form tablets. The tablets are then spray coated with a polymer solution containing dispersed L-threo-DOPS, sufficient to deliver the required immediate release dose.

3. An extended release hydrophilic matrix formulation prepared by wet granulation using a high shear mixer and filled into hard gelatin capsules containing:

| | |
|---|---|
| L-threo-DOPS | 100 to 800 mg |
| Hydroxypropylmethylcellulose (HPMC) | 5 to 45% |
| Lactose | 5 to 20% |
| Magnesium stearate | 0 to 1.5% |
| Silicon dioxide | 0 to 0.5% |
| Granulation fluid | q.s. |

The drug, polymer, and filler are dry blended in a high shear mixer for 5 minutes, at which time sufficient granulation fluid is added to produce a wet granulation that is subsequently dried, screened, blended with lubricant, and filled into hard gelatin capsules.

4. An extended release hydrophilic Matrix-formulation prepared by wet granulation using a high shear mixer and blended with an immediate release formulation containing the following before being filled into hard gelatin capsules:

| | |
|---|---|
| L-threo-DOPS | 25 to 300 mg |
| Lactose | 20 to 40% |
| Microcrystalline Cellulose | 5 to 15% |
| Magnesium stearate | 0 to 1.5% |
| Silicon dioxide | 0 to 0.5% |
| Granulation fluid | q.s. |

The drug and fillers are dry blended in a high shear mixer for 5 minutes, at which time sufficient granulation fluid is added to produce a wet granulation that is subsequently dried, screened, and blended with lubricant. An appropriate blend of the extended release formulation and the immediate release formulation are prepared and filled into hard gelatin capsules.

5. An extended release hydrophilic matrix formulation prepared by wet granulation using a fluidized bed granulator and compressed into tablets containing:

| | |
|---|---|
| L-threo-DOPS | 100 to 800 mg |
| Polyvinyl alcohol | 20 to 60% |
| Sodium Chloride | 10 to 30% |
| Lactose | 10 to 25% |
| Granulation fluid (e.g., Hydroxypropylcellulose, HPC, 5% solution) | q.s. |
| Magnesium stearate | 0 to 1.5% |
| Silicon dioxide | 0 to 0.5% |

The drug, polymer, and fillers are dry blended, and then granulated in a fluidized bed granulator using sufficient granulation fluid to produce a wet granulation that is subsequently dried, screened, blended with lubricant, and compressed to form tablets.

6. An extended release hydrophilic matrix formulation prepared by wet granulation using a fluidized bed granulator and compressed into tablets, onto which is applied additional L-threo-DOPS dispersed in an immediate release polymeric film coat containing:

| | |
|---|---|
| L-threo-DOPS | 25 to 300 mg |
| Ethylcellulose | 0 to 5.0% |
| Hydroxypropylmethylcellulose | 0 to 3.0% |
| Triethyl citrate | 0 to 2.0% |
| Aqueous ethanol | q.s. |

The drug, polymer, and fillers are dry blended, and then granulated in a fluidized bed granulator using sufficient granulation fluid to produce a wet granulation that is subsequently dried, screened, blended with lubricant, and compressed to form tablets. The tablets are then spray coated with a polymer solution containing dispersed L-threo-DOPS, sufficient to deliver the required immediate release dose.

7. An extended release hydrophilic matrix formulation prepared by wet granulation using a high shear mixer and filled into hard gelatin capsules containing:

| | |
|---|---|
| L-threo-DOPS | 100 to 800 mg |
| Polyvinyl alcohol | 20 to 60% |
| Sodium chloride | 10 to 30% |
| Lactose | 10 to 25% |
| Granulation fluid (hydroxypropylcellulose, HPC, 5% solution) | q.s. |
| Magnesium stearate | 0 to 1.5% |
| Silicon dioxide | 0 to 0.5% |

The drug, polymer, and fillers are dry blended in a high shear mixer for 5 minutes, at which time sufficient granulation fluid is added to produce a wet granulation that is subsequently dried, screened, blended with lubricant, and compressed to form tablets.

8. An extended release hydrophilic matrix formulation prepared by wet granulation using a high shear mixer and blended with an immediate release formulation containing the following before being filled into hard gelatin capsules:

| | |
|---|---|
| L-threo-DOPS | 25 to 300 mg |
| Lactose | 20 to 40% |
| Microcrystalline Cellulose | 5 to 15% |
| Magnesium stearate | 0 to 1.5% |
| Silicon dioxide | 0 to 0.5% |
| Granulation fluid | q.s. |

The drug and fillers are dry blended in a high shear mixer for 5 minutes, at which time sufficient granulation fluid is added to produce a wet granulation that is subsequently dried, screened, and blended with lubricant. An appropriate blend of the extended release formulation and the immediate release formulation are prepared and filled into hard gelatin capsules.

9. An extended release hydrophilic matrix formulation prepared by wet granulation using a fluidized bed granulator and compressed into tablets containing:

| | |
|---|---|
| L-threo-DOPS | 100 to 800 mg |
| Hydroxypropylmethylcellulose (HPMC) | 10 to 50% |
| Lactose | 10 to 25% |
| Dibasic calcium phosphate | 0 to 50% |
| Microcrystalline Cellulose | 0 to 25% |
| Granulation Fluid (Polyvinylpyrrolidone, PVP, 4% solution or Hydroxypropylmethylcellulose, HPMC, 3% solution) | q.s. |
| Magnesium stearate | 0 to 1.5% |
| Silicon dioxide | 0 to 5.0% |

The drug, polymer, and fillers are dry blended, and then granulated in a fluidized bed granulator using sufficient granulation fluid to produce a wet granulation that is subsequently dried, screened, blended with lubricant, and compressed to form tablets.

10. An extended release hydrophilic matrix formulation prepared by wet granulation using a high fluidized bed granulator and compressed into tablets, onto which is applied additional L-threo-DOPS dispersed in an immediate release polymeric film coat containing:

| | |
|---|---|
| L-threo-DOPS | 25 to 300 mg |
| Ethylcellulose | 0 to 5.0% |
| Hydroxypropylmethylcellulose | 0 to 3.0% |
| Triethyl citrate | 0 to 2.0% |
| Aqueous ethanol | q.s. |

The drug, polymer, and fillers are dry blended, and then granulated in a fluidized bed granulator using sufficient granulation fluid to produce a wet granulation that is subsequently dried, screened, blended with lubricant, and compressed to form tablets. The tablets are then spray coated with a polymer solution containing dispersed L-threo-DOPS, sufficient to deliver the required immediate release dose.

The invention claimed is:

1. A pharmaceutical formulation comprising an effective amount of threo-3-(3,4-dihydroxyphenyl)serine, a derivative thereof, or a pharmaceutically-acceptable salt thereof in the form of particles or granules that are coated with or embedded in a slowly soluble polymeric membrane effective for dissolution controlled, extended release of the threo-3-(3,4-dihydroxyphenyl)serine, a derivative thereof, or a pharmaceutically-acceptable salt thereof over a period of time of at least 6 hours, the formulation being adapted for oral delivery.

2. The pharmaceutical formulation of claim 1, wherein the slowly soluble polymeric membrane comprises one or more materials selected from the group consisting of ethylcellulose, cellulose acetate phthalate, acrylic resins, methacrylate hydrogels, methylmethacrylate, polymethacrylate, polylactic acid, polyvinyl chloride, hydroxypropylmethylcellulose, polyethylene glycols, carboxymethylcellulose, sodium carboxymethylcellulose, and mixtures thereof.

3. The pharmaceutical formulation of claim 1, wherein the particles or granules of the threo-3-(3,4-dihydroxyphenyl)serine, a derivative thereof, or a pharmaceutically-acceptable salt thereof are non-pareil seeds having the threo-3-(3,4-dihydroxyphenyl)serine, a derivative thereof, or a pharmaceutically-acceptable salt thereof applied to a surface thereof.

4. The pharmaceutical formulation of claim 1, further comprising threo-3-(3,4-dihydroxyphenyl)serine, a derivative thereof, or a pharmaceutically-acceptable salt thereof in an immediate release form.

5. The pharmaceutical formulation of claim 4, wherein the formulation provides for maximal release of the immediate release form within about 1 to about 3 hours after administration, and provides for maximal release of the extended release form between about 6 to about 24 hours after administration.

6. The pharmaceutical formulation of claim 4, wherein one or both of the extended release form and immediate release form of the threo-3-(3,4-dihydroxyphenyl)serine, or a derivative or pharmaceutically-acceptable salt thereof, is released at a rate that is independent of the pH in the gastrointestinal tract.

7. The pharmaceutical formulation of claim 4, wherein the formulation comprises 45-85% by weight of the threo-3-(3,4-dihydroxyphenyl) serine, a derivative thereof, or a pharmaceutically-acceptable salt thereof, in the extended release form and 15-55% by weight of the threo-3-(3,4-dihydroxyphenyl)serine, a derivative thereof, or a pharmaceutically-acceptable salt thereof, in the immediate release form.

8. The pharmaceutical formulation of claim 4, wherein the extended release form further comprises an osmotically active salt.

9. The pharmaceutical formulation of claim 1, further comprising an excipient selected from the group consisting of lubricants, channeling agents, surfactants, fillers, coating materials, and combinations thereof.

10. The pharmaceutical formulation of claim 9, wherein the excipient is selected from the group consisting of silicon dioxide, magnesium stearate, sodium lauryl sulfate, sodium taurocholate, polysorbate, lactose, hydroxypropylmethylcellulose, ethylcellulose, triethyl citrate, microcrystalline cellulose, polyvinyl alcohol, sodium chloride, dibasic calcium phosphate, polyvinylpyrrolidone, and mixtures thereof.

11. The pharmaceutical formulation of claim 1, wherein the pharmaceutical formulation is suitable for once-daily administration.

12. The pharmaceutical formulation of claim 1, wherein the pharmaceutical formulation is suitable for twice- or three-times daily administration.

13. A pharmaceutical formulation comprising an effective amount of threo-3-(3,4-dihydroxyphenyl)serine, a derivative thereof, or a pharmaceutically-acceptable salt thereof surrounded by a water-insoluble polymeric material effective for diffusion controlled, extended release of the threo-3-(3,4-dihydroxyphenyl)serine, a derivative thereof, or a pharmaceutically-acceptable salt thereof over a period of time of at least 6 hours, wherein the formulation is in the form of a reservoir device or a matrix device, and wherein the formulation is adapted for oral delivery.

14. The pharmaceutical formulation of claim 13, further comprising threo-3-(3,4-dihydroxyphenyl)serine, a derivative thereof, or a pharmaceutically-acceptable salt thereof in an immediate release form.

15. The pharmaceutical formulation of claim 14, wherein the formulation provides for maximal release of the immediate release form within about 1 to about 3 hours after administration, and provides for maximal release of the extended release form between about 6 to about 24 hours after administration.

16. The pharmaceutical formulation of claim 14, wherein one or both of the extended release form and immediate release form of the threo-3-(3,4-dihydroxyphenyl)serine, or a derivative or pharmaceutically-acceptable salt thereof, is released at a rate that is independent of the pH in the gastrointestinal tract.

17. The pharmaceutical formulation of claim 14, wherein the formulation comprises 45-85% by weight of the threo-3-(3,4-dihydroxyphenyl)serine, a derivative thereof, or a pharmaceutically-acceptable salt thereof, in the extended release form and 15-55% by weight of the threo-3-(3,4-dihydroxyphenyl)serine, a derivative thereof, or a pharmaceutically-acceptable salt thereof, in the immediate release form.

18. The pharmaceutical formulation of claim 13, wherein the extended release form further comprises an osmotically active salt.

19. The pharmaceutical formulation of claim 13, further comprising an excipient selected from the group consisting of lubricants, channeling agents, surfactants, fillers, and combinations thereof.

20. The pharmaceutical formulation of claim 19, wherein the excipient is selected from the group consisting of silicon dioxide, magnesium stearate, sodium lauryl sulfate, sodium taurocholate, polysorbate, lactose, hydroxypropylmethylcellulose, ethylcellulose, triethyl citrate, microcrystalline cellulose, polyvinyl alcohol, sodium chloride, dibasic calcium phosphate, polyvinylpyrrolidone, and mixtures thereof.

21. The pharmaceutical formulation of claim 13, wherein the pharmaceutical formulation is suitable for once-daily administration.

22. The pharmaceutical formulation of claim 13, wherein the pharmaceutical formulation is suitable for twice- or three-times daily administration.

23. The pharmaceutical formulation of claim 13, wherein the formulation is in the form of a reservoir device wherein the threo-3-(3,4-dihydroxyphenyl)serine, a derivative thereof, or a pharmaceutically-acceptable salt thereof is in a core surrounded by the water insoluble polymeric material.

24. The pharmaceutical formulation of claim 23, wherein the water insoluble polymeric material is selected from the group consisting of hydroxypropylcellulose/polyvinyl acetate combinations, polyethylene glycol/ethylcellulose combinations, ethylcellulose, poly(hydroxymethacrylate), and combinations thereof.

25. The pharmaceutical formulation of claim 13, wherein the formulation is in the form of a matrix device wherein the threo-3-(3,4-dihydroxyphenyl)serine, a derivative thereof, or a pharmaceutically-acceptable salt thereof is dispersed in the water insoluble polymeric material.

26. The pharmaceutical formulation of claim 25, wherein the water insoluble polymeric material is selected from the group consisting of hydrated methylcellulose, carnauba wax and stearyl alcohol combinations, carbopol, glyceryl tristearate, methyl acrylate/methyl methacrylate combinations, polyvinyl chloride, polyethylene, and combinations thereof.

27. The pharmaceutical formulation of claim 13, wherein the water insoluble polymeric material further comprises an amount of a water soluble material that is adapted to solubilize in the presence of water such that the water insoluble polymeric material surrounding the threo-3-(3,4-dihydroxyphenyl)serine, a derivative thereof, or a pharmaceutically-acceptable salt thereof exhibits a porosity.

28. The pharmaceutical formulation of claim 27, wherein the water soluble material comprises a combination of ethylcellulose and methylcellulose.

29. A pharmaceutical formulation in an extended release form comprising: an effective amount of threo-3-(3,4-dihydroxyphenyl)serine, or a derivative or pharmaceutically-acceptable salt thereof, a coating/matrix material, a channeling agent, and a filler, wherein the formulation provides continuous release of threo-3-(3,4-dihydroxyphenyl)serine, or a derivative or pharmaceutically-acceptable salt thereof, over a period of at least 6 hours, and wherein the formulation is adapted for oral delivery.

30. The pharmaceutical formulation of claim 29, wherein the threo-3-(3,4-dihydroxyphenyl)serine, or a derivative or pharmaceutically-acceptable salt thereof, is provided in a core surrounded by a water-insoluble polymeric material.

31. The pharmaceutical formulation of claim 29, wherein the coating/matrix material is selected from the group consisting of shellacs, beeswax, glyceryl monostearate, glyceryl palmostearate, stearyl alcohol, ethylcellulose, cellulose acetate phthalate, acrylic resins, methacrylate hydrogels, methylmethacrylate, polymethacrylate, polylactic acid, polyvinyl chloride, hydroxypropylmethylcellulose, polyethylene glycols, carboxymethylcellulose, sodium carboxymethylcellulose, and mixtures thereof.

32. The pharmaceutical formulation of claim 29, wherein the channeling agent is silicon dioxide.

33. The pharmaceutical formulation of claim 29, wherein the filler is selected from the group consisting of lactose, sodium chloride, triethyl citrate, and combinations thereof.

34. The pharmaceutical formulation of claim 29, further comprising an excipient selected from the group consisting of surfactants, lubricants, granulating agents, and combinations thereof.

35. The pharmaceutical formulation of claim 34, comprising a surfactant selected from the group consisting of sodium lauryl sulfate, sodium taurocholate, polysorbates, and combinations thereof.

36. The pharmaceutical formulation of claim 34, comprising the lubricant magnesium stearate.

37. The pharmaceutical formulation of claim 29, further comprising an effective amount of threo-3-(3,4-dihydroxyphenyl)serine, a derivative thereof, or a pharmaceutically-acceptable salt thereof, in an immediate release form.

38. The pharmaceutical formulation of claim 37, wherein one or both of the extended release form and the immediate release form of the threo-3-(3,4-dihydroxyphenyl)serine, or a derivative or pharmaceutically-acceptable salt thereof, is released at a rate that is independent of the pH in the gastrointestinal tract.

39. The pharmaceutical formulation of claim 37, wherein the formulation provides for maximal release of the immediate release form within about 1 to about 3 hours after administration, and provides for maximal release of the extended release form between about 6 to about 24 hours after administration.

40. The pharmaceutical formulation of claim 37, wherein the formulation comprises 45-85% by weight of the threo-3-(3,4-dihydroxyphenyl)serine, a derivative thereof, or a pharmaceutically-acceptable salt thereof, in the extended release form and 15-55% by weight of the threo-3-(3,4-dihydroxyphenyl)serine, a derivative thereof, or a pharmaceutically-acceptable salt thereof, in the immediate release form.

41. The pharmaceutical formulation of claim 29, wherein the formulation is suitable for once daily administration.

42. The pharmaceutical formulation of claim 29, wherein the formulation is suitable for twice a day or three times a day administration.

* * * * *